(12) United States Patent
Kulah et al.

(10) Patent No.: US 9,630,007 B2
(45) Date of Patent: Apr. 25, 2017

(54) ENERGY HARVESTING COCHLEAR IMPLANT

(76) Inventors: Haluk Kulah, Ankara (TR); Nebil Goksu, Ankara (TR); Levent Beker, Ankara (TR)

( * ) Notice: Subject to any disclaimer, the term of this patent is extended or adjusted under 35 U.S.C. 154(b) by 24 days.

(21) Appl. No.: 14/355,213

(22) PCT Filed: Dec. 2, 2011

(86) PCT No.: PCT/TR2011/000237
§ 371 (c)(1),
(2), (4) Date: Apr. 30, 2014

(87) PCT Pub. No.: WO2013/081560
PCT Pub. Date: Jun. 6, 2013

(65) Prior Publication Data
US 2014/0303688 A1 Oct. 9, 2014

(51) Int. Cl.
*A61N 1/36* (2006.01)
*A61N 1/378* (2006.01)
*H01L 41/113* (2006.01)
*H02N 2/18* (2006.01)
(Continued)

(52) U.S. Cl.
CPC ....... *A61N 1/36032* (2013.01); *A61N 1/3785* (2013.01); *H01L 41/1136* (2013.01); *H02N 2/188* (2013.01); *H04R 25/606* (2013.01); *H04R 17/00* (2013.01)

(58) Field of Classification Search
CPC .............. A61N 1/0541; A61N 1/36032; A61N 1/378–1/3787
See application file for complete search history.

(56) References Cited

U.S. PATENT DOCUMENTS

| 3,456,134 A | 7/1969 | Ko |
| 5,856,722 A * | 1/1999 | Haronian ................. H03H 9/50 310/309 |
| 6,261,224 B1 | 7/2001 | Adams et al. |

(Continued)

OTHER PUBLICATIONS

Harada et al: "Fish-bone-structured acoustic sensor toward silicon cochlear systems", Proceedings of SPIE, Jan. 1, 1998, pp. 266-275, vol. 3514, XP002288947.

(Continued)

*Primary Examiner* — Eric D. Bertram
(74) *Attorney, Agent, or Firm* — Gokalp Bayramoglu

(57) ABSTRACT

The invention is related to a totally implantable cochlear implant having a transducer which is a piezoelectric vibration energy harvester to be mounted on the ossicular chain or the tympanic membrane to detect the frequency of oscillations and generate the required voltage to stimulate the relevant auditory nerves. The invention enables patients' continuous access to sound, since it eliminates the outside components of conventional cochlear implants. The invention also eliminates the problem of battery need, since the transducer generates voltage required to stimulate auditory nerves from the vibrations of ossicular chain. The transducer is fabricated using Microelectromechanical Systems (MEMS) fabrication techniques. The invention incorporates of two main parts, a transducer acting both as a frequency detector and an energy harvester, and electrodes to stimulate the auditory nerve inside the cochlea.

9 Claims, 4 Drawing Sheets

(51) Int. Cl.
*H04R 25/00* (2006.01)
*H04R 17/00* (2006.01)

(56) References Cited

U.S. PATENT DOCUMENTS

| | | | |
|---|---|---|---|
| 6,264,603 B1 | 7/2001 | Kennedy | |
| 8,634,924 B1* | 1/2014 | Ko et al. | 607/57 |
| 2003/0012390 A1* | 1/2003 | Franks | A61N 1/36032 381/114 |
| 2005/0113633 A1 | 5/2005 | Blau et al. | |
| 2005/0245990 A1* | 11/2005 | Roberson | 607/57 |
| 2010/0295419 A1 | 11/2010 | Fujii | |

OTHER PUBLICATIONS

P. D. Mitcheson, et al: "Architectures for vibration driven micropower generators", Journal of Microelectromechanical Systems, vol. 13, No. 3, Jun. 2004.

C.B. Williams and R.B. Yates: "Analysis of micro-electric generator for microsystems", 8th International Conference on Solid-State Sensors, Actuators, and Microsystems (Transducers '95), pp. 369-372, Jun. 1995.

S. Roundy, P.K. Wright and J. Rabaey: "A study of low level vibrations as a power source for wireless sensor nodes", Computer Communications, vol. 26, pp. 1131-1144, 2003.

A. C. R. Grayson, et al: "A BioMEMS review: MEMS technology for physiologically integrated devices", Proceedings of the IEEE, vol. 92, No. 1, Jan. 2004.

A. Nisar, et al: "MEMS-based micropumps in drug delivery and biomedical applications", Sensors and Actuators B:Chemical, vol. 130, No. 2, pp. 917-942, 2008.

P. C. Loizou: "Introduction to cochlear implants", IEEE Engineering in Medicine and Biology, vol. 18, No. 1, pp. 32-42, Jan. 1999.

B.S. Lee, et al: "Piezoelectric MEMS generators fabricated with an aerosol deposition PZT thin film", Journal of Micromechanics and Microengineering, vol. 19, No. 6, Jun. 2009.

E. E. Aktakka, H. Kim and K. Najafi: "Wafer level fabrication of high performance MEMS using bonded and thinned bulk piezoelectric substrates", 15th International Conference on Solid-State Sensors, Actuators, and Microsystems (Transducers '09). pp. 849-852, Jun. 2009.

M.K. Cosetti and S.B. Waltzman: "Cochlear implants: current status and future potential", Expert Review of Medical Devices, vol. 8, No. 3, pp. 389-401, May 2011.

\* cited by examiner

ENERGY HARVESTING COCHLEAR IMPLANT

TECHNICAL FIELD OF INVENTION

The invention is related to a totally implantable cochlear implant having a transducer which is a vibration energy harvester using piezoelectric effect and to be mounted on the ossicular chain or the tympanic membrane to detect the frequency of oscillations and generate the required impulse for the stimulation of the relevant auditory nerves. Therefore, the invention eliminates the components of the cochlear implant outside the body and the need for battery. The transducer is fabricated using Micro-Electro-Mechanical Systems (MEMS) fabrication techniques and coated with a biocompatible material.

BACKGROUND OF INVENTION

With the advances in MEMS technology it is possible to fabricate small size and high performance electromechanical energy harvesters converting ambient vibration to electrical potential using MEMS fabrication techniques [1]. Electromagnetic, electrostatic, and piezoelectric transduction mechanisms are the most popular approaches for vibration-based energy harvesting [2]. Among these transduction mechanisms piezoelectric energy harvesting is more attractive due to high voltage output and no need of separate voltage source to initiate the conversion process as in the electrostatic converters [3].

MEMS technology has recently become crucial for biomedical implants as it enables the implementation of smart devices with features that range in size from millimeters to sub-micrometers [4]. Especially in the last two decades, integration of MEMS technology with biomedical industry attracted the attention of many researchers [5]. One of the most promising applications of MEMS technology for biomedical applications is hearing aids.

Hearing impairment is a common disease affecting the patient's quality of life by limiting the social interaction of him/her with the environment. Several types of diseases and various solution methods have been proposed in the past. Being one of the most popular solutions, cochlear implants provide effective and aesthetic solutions for patients suffering hearing impairment. Cochlear implants have three main components in common: a microphone, a signal processor, and an electrode [6]. The microphone converts the incoming sound waves to electrical signals. The signal processor calibrates the amplitude and frequency of these signals, and then transfers them to the electrode, where the corresponding auditory nerves are stimulated.

Microphone is the most critical component of cochlear implants since it converts the acoustic pressure waves into electrical signals. However since the microphone is mounted outside the body it prevents patients' continuous access to sound (while swimming, showering etc.), and constitutes a potential for hardware damage and decreases cosmetic appeal [9].

Up to now various devices to replace the microphone component of cochlear implants which is mounted outside of the body and to reduce the battery need of cochlear implants have been reported.

U.S. Pub. No. 20030012390 reports a vibration detector device suitable for use instead of a microphone in cochlear implants. This device incorporates resonator bars with varying resonation frequencies due to varying thicknesses. Although the microphone used in conventional cochlear implants which is mounted outside the body can be reduced by using the suggested device, this device cannot eliminate the need for battery.

U.S. Pat. No. 6,264,603 describes a vibration detector for sensing the vibration amplitude and direction. The reported device is not capable of generating energy for reducing the battery need of cochlear implants.

US. Pub. No. 20050113633 describes an electromechanical converter converting vibration of ossicles to electrical signals. It is reported that the use of thin elliptic piezoelectric element reduces the power consumption of the device. However, since a single elliptic thin element is used for detecting vibrations, it is not possible to make use of resonance phenomena for increasing the voltage output of piezoelectric element. Therefore stimulation of the auditory nerves without processing the generated signals with electronic unit is not possible.

U.S. Pat. No. 6,261,224 describes a piezoelectric structure coupled to an auditory element such as malleus to be used as both an actuator and a sensor. It is noted that the device is capable of generating a potential due to vibrations of the auditory elements; however the generated voltage is processed with the electronic unit of the implantable system. The generated voltage is used for detecting the frequency of the vibrations and dissipated at the signal processing step. Therefore, again the reported device is not capable of reducing the battery need of conventional cochlear implants.

Another device to be used as a frequency detector is disclosed in U.S. Pat. No. 5,856,722. In this document, a microelectromechanical system is proposed. However this device again does not offer a solution to the power consumption problem of implants.

The need of a battery in cochlear implants is a problematic issue. Patients have to carry a battery pack and recharge them periodically to power up the cochlear implant system. U.S. Pat. No. 3,456,134 describes a piezoelectric energy converter for electronic implants. The device is aimed to convert vibrations due to body motions into electrical energy for driving the implants. However, the suggested device is not capable of converting the acoustical pressure waves or vibrations of ossicular chain to meaningful potential output. Therefore this device cannot be used as a microphone to sense the frequency of acoustical sound pressure waves.

Recently high performance energy harvester devices are developed by using piezoelectric principle. Lee et al. fabricate an aerosol deposited PZT micro cantilever beam operated at 214 Hz gives up to 4,127 V output voltage, which shows that MEMS piezoelectric energy scavenger can be used for both sensing the frequency and generating potential required for 250 Hz-4000 Hz frequency range [7].

Based on the present state of art, it is therefore an object to provide a totally implantable device, capable of detecting the frequency of the acoustic sound pressure waves vibrating the tympanic membrane and reducing the battery need of the cochlear implant device, and that provides long-term stability and biocompatibility.

The object is solved with a totally implantable device mounted to ossicular chain, having multiple cantilever beams with predetermined natural frequencies to sense the incoming vibrations and generate required voltage by making use of resonance phenomena to stimulate the auditory nerves.

BRIEF DESCRIPTION OF THE INVENTION

The present invention provides a method and apparatus for improving the impaired hearing of a patient by utilizing a totally implantable cochlear implant. The invention incorporates two main parts, a transducer acting both as a frequency detector and an energy harvester, and electrodes to stimulate the auditory nerve inside the cochlea.

Incoming acoustical sound pressures are converted to vibrations at the tympanic membrane of human ear. Ossicular chain amplifies these vibrations and transfers these vibrations to oval window. The transducer according to this invention is preferably mounted to the ossicular chain to sense the frequency of the vibrations of the incoming sound pressure waves. These vibrations are converted to electricity by piezoelectric principle. This invention uses the generated electrical potential to stimulate the auditory nerves. The transducer according to this invention does not need an electronic unit to stimulate the auditory nerves since it has a mechanical frequency selective structure (i.e. cantilever beams of predetermined natural frequencies). Vibrations of a cantilever beam with a frequency equal to its natural frequency would result in generating a potential output required to stimulate the auditory nerve of the same frequency band. By connecting the output of the mentioned cantilever beam to the auditory nerve of the same frequency band, stimulation will occur as voltage is generated.

DETAILED DESCRIPTION OF THE INVENTION AND PREFERRED EMBODIMENTS

In the following detailed description, reference is made to the accompanying drawings such that, FIG. 1 is a schematic view of the human ear;

Figure 1:
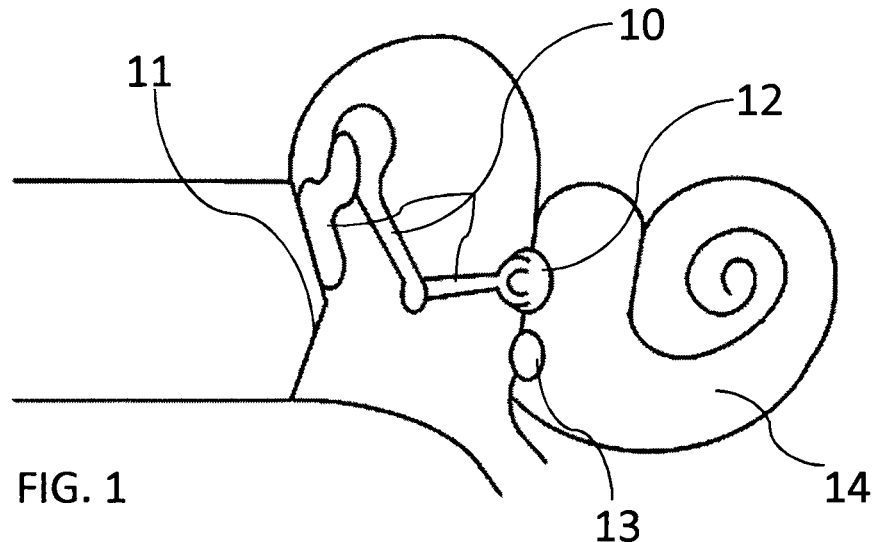
Figure 10:
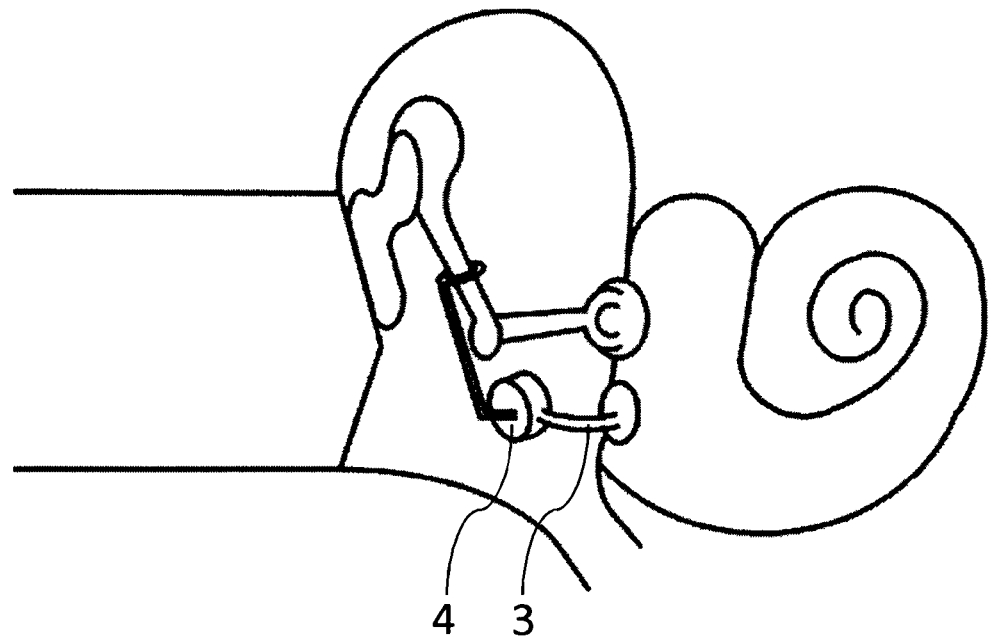

FIG. 10 is a schematic view of a transducer installed on the incus with partially shown electrodes mounted into cochlea through round window The numerals referred to in the following description correspond to the following, 1. Microphone
2. Signal processor
3. Cochlear electrode
4. Transducer
5. Base
6. Cantilever beam
6a. Free end
6b. Fixed end
7. Piezoelectric piece
8. Harvester electrode
9. Tip mass
10. Ossicular chain
11. Tympanic membrane
12. Oval window
13. Round window
14. Cochlea S. Neutral axis Referring to FIG. 1, in a healthy ear, incoming acoustic sound pressure waves cause vibration of the tympanic membrane (11). The ossicular chain (10) amplifies these vibrations and transfers them to the oval window (12). The vibrations are than transmitted onto the fluid in the cochlea (14), with the round window (13) providing space for said fluid to vibrate. The frequency of vibrations set the relevant regions of the basilar membrane in motion. This motion causes the hair cells to generate a voltage. Auditory nerves are stimulated with the generated voltage and hearing of the corresponding frequency occurs.

Sensorineural hearing loss is a type of hearing impairment where damaged or missing hair cells in the cochlea (14) prevent the stimulation of auditory nerves. Conventional cochlear implants allow patients to stimulate the auditory nerves on behalf of hairy cells. Therefore patients can hear with the help of cochlear implants and interact with his/her environment.

Figure 2:
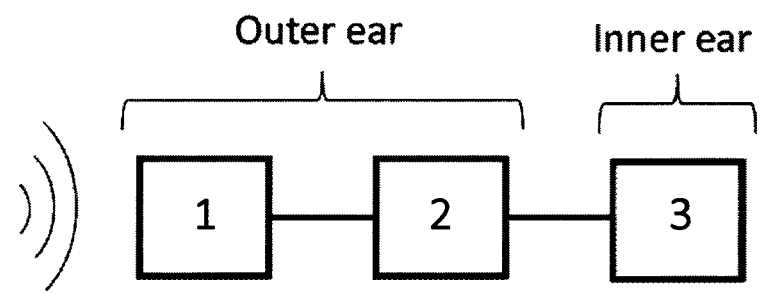
FIGS. 2 and 3 are schematic views depicting components of a cochlear implant according to the prior art.
Figure 3:
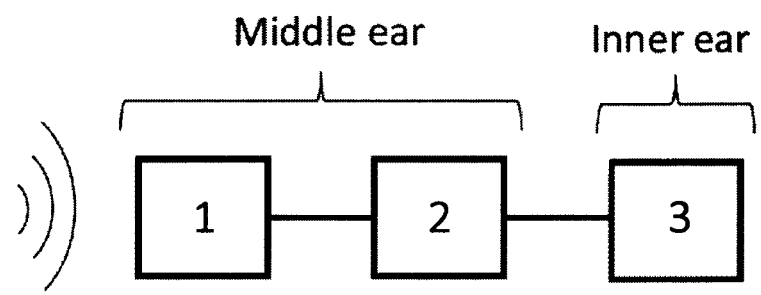

Referring to FIG. 2, current commercial cochlear implants have three main parts, microphone (1), signal processor (2) and electrode (3). In conventional cochlear implants microphone (1) components are usually mounted to the outer ear, which is not desirable due to aesthetic and reliability issues. Some of the recently developed devices eliminate the necessity of a microphone (1) or a signal processor (2) to be mounted outside the body, as seen in FIG. 3. However neither of these devices eliminates the need of a battery. The present invention consists of two main parts as in FIG. 4. First part is an electromechanical transducer (4) which can be coupled directly with the second part, a cochlear electrode (3) placed into the cochlea (14) to stimulate the auditory nerves. The present invention incorporates a transducer (4) acting both as an energy harvester and a frequency detector replacing the microphone (1) and signal processor (2) used in conventional cochlear implants. The battery requirement of the conventional cochlear implants is also eliminated due to energy harvesting property of the proposed invention.

The transducer (4) according to the present invention consists of multiple cantilever beams (6) with predetermined natural frequencies and is capable of converting input vibrations to electrical signals using piezoelectric pieces (7) placed to the fixed end of the beams (6b). The number of cantilever beams (6) and the natural frequency of each beam can be altered depending on patients' specific needs. If the apex of the cochlea (14) is damaged, said transducer (4) can consist of beams (6) corresponding to low frequencies. In a similar manner, if the base of the cochlea (14) is damaged the transducer (4) can consist of beams (6) corresponding to high frequencies. The transducer (4) is mounted to the ossicular chain (10) in order to sense the vibrations. Therefore, by using a totally implantable system, patients will have a continuous access to sound, and damage risks of the outer components and aesthetic issues will be suppressed.

Incoming acoustical sound pressure waves are converted to vibrations at the tympanic membrane (11). These vibrations are amplified by ossicular chain (10). The frequency and the amplitude of these vibrations comprise the information of incoming sound. In a preferred embodiment (FIG. 11), by mounting the transducer (4) to the incus, acoustical sound pressure waves are transferred to the transducer (4) by vibrations of ossicular chain (10). Due to the resonant property of the structure, when the input vibration frequency is matched with the natural frequency of the corresponding cantilever beam (6) of the transducer (4), that beam (6) will achieve a maximum deflection at the tip and a maximum stress at the fixed end of the beam (6b). The piezoelectric piece (7) on the beam (6b) vibrating at its resonance frequency provides a voltage output which is large enough to stimulate the auditory nerve. The voltage output of the beam (6) stimulates the corresponding auditory nerve, i.e. the auditory nerve which the natural frequency of the cantilever beam (6) is matched to the auditory nerve of the same frequency range.

The voltage outputs generated by the piezoelectric pieces (7) associated with each cantilever beam (6) vibrating near its natural frequency are higher than a threshold voltage value. For the transducer (4) to be employed in a cochlear implant, said threshold voltage value is the threshold voltage value required to stimulate the auditory nerve.

The transducer is a MEMS structure which can be fabricated on a single crystal silicon substrate. Therefore the fabricated device dimensions are in the orders of micrometers or millimeters. Fabricated transducer (4) is coated with a biocompatible coating of parylene-c or another biocompatible material in order to prevent infections. Also it is possible with MEMS technology to produce an array of beams (6) layer by layer without increasing the thickness of the device considerably. Therefore it is possible to increase the number of cantilever beams (6) in order to increase sensitivity of hearing, i.e. providing cantilever beams (6) corresponding to a large number of narrow frequency bands. Another advantage of MEMS fabrication technology is that the rectifier circuitry can also be implemented on the silicon substrate. Therefore, if there is a need for modification of the output voltage, rectifier circuitry can be built to operate with the structure and if the generated voltage level is not enough to power up this circuitry, an auxiliary battery can be used for compensation. Even in this case, the overall system power consumption is much less than the conventional hearing implants, and the battery lifetime of such a system is much longer than the patient's life span, avoiding the necessity to replace the battery.

Main advantage of the present invention is that it reduces the need of a battery to power up the cochlear implant. The transducer (4) works as an energy harvester. Harvested energy is used to stimulate the auditory nerves. Therefore the present invention does not need a battery. Piezoelectric principle is used to generate required voltage output by bonding piezoelectric pieces (7) to the cantilever beams (6). The primary advantage of piezoelectric transduction mechanism is the higher voltage output potential [3] than electromagnetic and electrostatic principle employed in energy harvesters. Also there is a considerable development in the process of the integration of piezoelectric materials (7) both as thin films [7] and bulk piezoelectric thick films [8]. Therefore suitable use of piezoelectric pieces (7) results in both a voltage output high enough to stimulate the auditory nerves and an implantable system without batteries.

Figure 5:
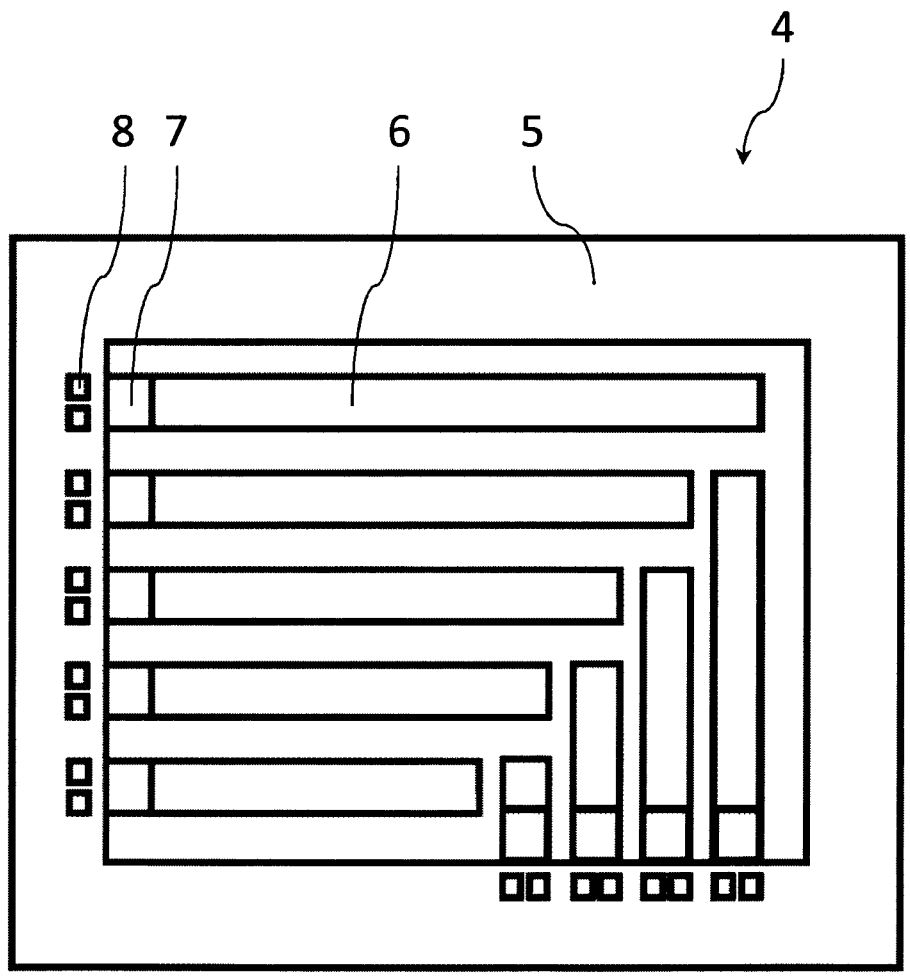
FIG. 5 depicts a transducer according to the invention.
Figure 6A:
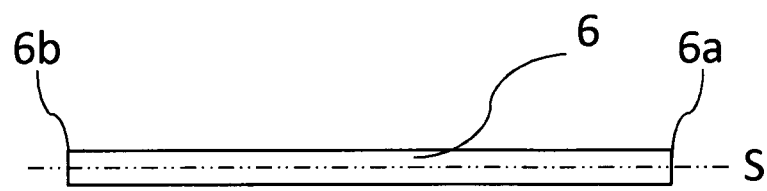
FIG. 6a is a side view of a beam of a transducer according to the invention in equilibrium position.
Figure 6B:
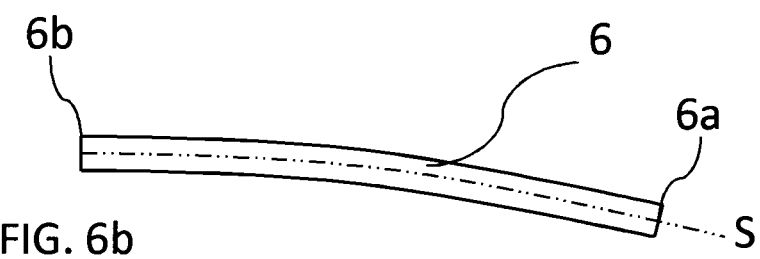
FIG. 6b is a side view of the beam in FIG. 6a in a disturbed position.

The transducer (4) for converting acoustic waves to voltage outputs wherein each voltage output corresponds to a particular frequency band of the incoming acoustic waves, essentially comprises,
  at least one base (5) attached onto a vibrating element of the auditory system,
  an array of cantilever beams (6) with one free end (6a) and one fixed end (6b) attached to said base (5), each having a predetermined natural frequency corresponding to the frequencies that the patient is not able to perceive,
  a piezoelectric piece (7) bonded to said cantilever beams (6), as depicted in FIG. 5. The transducer (4) further comprises at least one harvester electrode (8) associated with every cantilever beam (6) in order to harvest the voltage produced by the piezoelectric pieces (7).

The beams (6) vibrate in transverse direction thus providing space for large amplitude vibrations and a high stress in regions around the fixed end (6b).

A piezoelectric piece (7) is positioned on a beam (6) such that said piezoelectric piece (7) is on an outer surface of said beam (6) that is farthest along the direction of vibration from the neutral axis (S) of the beam (6) and near the fixed end (6b) so that said piezoelectric piece (7) experiences the maximum possible stress. Thus the piezoelectric piece (7) provides a voltage high enough to provide the impulse required to stimulate the cochlear nerve without the aid of a power supply.

Figure 4:
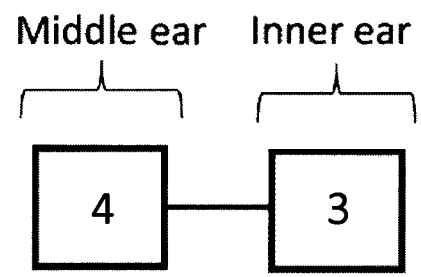
FIG. 4 is a schematic view depicting components of a cochlear implant according to the present invention.

A transducer (4) for a cochlear implant according to the invention is depicted in FIG. 4. Such a transducer (4) is to be mounted on a vibrating element of the auditory system such as the tympanic membrane (11) or one of the ossicles (10) and connected to at least one cochlear electrode (3) attached to the auditory nerve.

Figure 7:
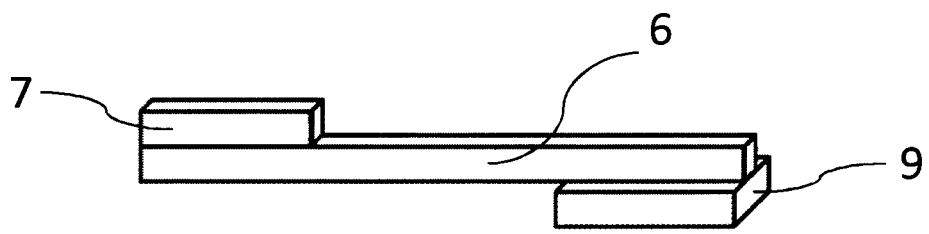
FIG. 7 depicts a beam of a transducer according to the invention in detail.
Figure 8:
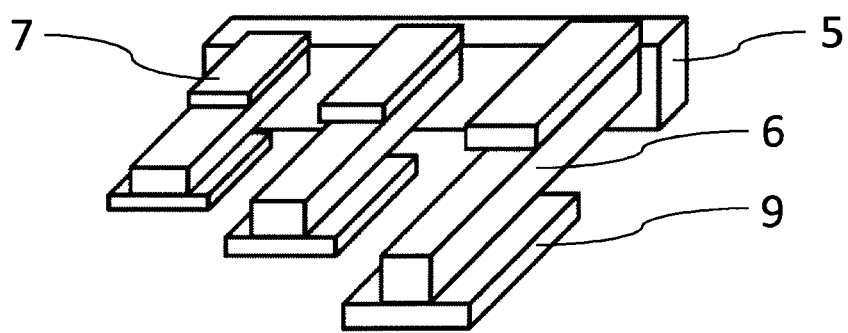
FIG. 8 is a partial view of a transducer according to the invention, depicting exemplary beams in detail.

The natural frequency of a beam (6) is generally determined by the thickness, width and length of the beams (6). However, to obtain beams (6) with low frequencies, a tip mass (9) can be attached on the free end (6a) of the desired beams (6), in order to avoid increasing the size of the transducer (4). Such a beam (6) incorporating a tip mass (9) is depicted in FIG. 7. In FIG. 8, beams (6) having different natural frequencies determined by both the use of a weight (9) and the adjustment of length and thickness are depicted.

The predetermined natural frequencies of the cantilever beams (6) to be employed in a cochlear implant according to this invention are determined according to the patients' needs. Thus, the predetermined natural frequencies of the cantilever beams (6) correspond to the frequencies that the patient is unable to perceive.

Figure 9:
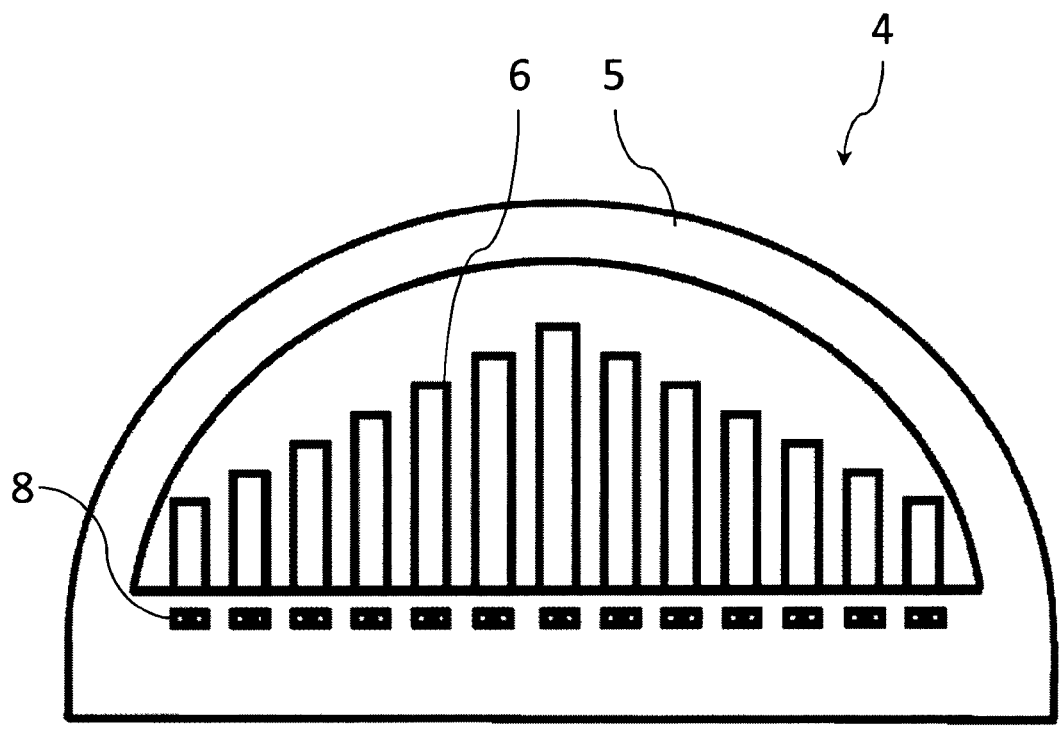
FIG. 9 depicts another transducer according to the invention.

The shape of the base (5) of the transducer (4) is determined according to which vibrating element of the auditory system that the transducer (4) is to be attached. An embodiment of the invention employing rectangular base (5) is depicted in FIG. 5 while another embodiment employing a semicircular base (5) is depicted in FIG. 9. The geometry of the base (5) is such that it fits best on the vibrating element of the auditory system used, so that both the complexity of surgery is decreased and vibration gain (amplitude and acceleration) of the transducer (4) is increased.

In an embodiment of the invention, in order to increase the voltage output of the transducer (4), more than one beam (6) having the same natural frequency are employed as can be seen in FIG. 9. The voltage output of the transducer (4) corresponding to a given frequency is directly proportional to the number of beams (6) having a natural frequency equal to that given frequency.

The transducer (4) according to the invention can be fabricated by
  providing a silicon wafer,
  bonding piezoelectric materials to the silicon wafer
  masking and etching of substrate to fabricate said cantilever beams (6) having the desired natural frequency,
  dicing of base (5) and release from silicon wafer The perceived frequencies can be increased by increasing the number of beams (6) in a transducer (4). Accordingly, in an embodiment of the invention, multiple bases (5) having beams (6) of different natural frequencies are bonded on top of each other forming a layered transducer (4) by using conventional bonding techniques used in MEMS technology. The thickness of the bonding layer and the gap between the layers are arranged such that the tip displacements of the cantilever beams (6) in consecutive layers do not interfere with each other.

Preferred Embodiment of the Invention

In a preferred embodiment of the invention a cochlear implant which comprises a transducer (4) and a cochlear electrode (3) connecting the transducer (4) to the auditory nerve is employed for converting acoustic waves to voltage outputs, to be used to stimulate the auditory nerve in a cochlear implant. Each of said voltage outputs corresponds to a particular frequency band of the incoming acoustic waves. The transducer (4) consists of

- at least one base (5) attached onto a vibrating element of the auditory system that vibrates under the influence of the incoming acoustic waves,
- an array of cantilever beams (6) each with one free end (6a) and one fixed end (6b) attached to said base (5), and each having a predetermined natural frequency,
- a piezoelectric piece (7) bonded to each of said cantilever beams (6) and
- at least one harvester electrode (8) associated with every cantilever beam (6) to harvest the voltage produced by the piezoelectric pieces (7) and connected to the cochlear electrode (3) to transmit said voltage to the cochlear electrode (3).

The method for converting acoustic waves to voltage outputs comprises the steps

- exposing said cantilever beams (6) to vibrations produced on said vibrating element of the auditory system under the influence of the incoming acoustic waves and
- generating voltage outputs due to piezoelectricity, at the piezoelectric pieces (7) associated with every vibrating cantilever beam (6).

The cochlear implant according to the invention can operate without the need of extra batteries. The required energy is produced by the piezoelectric pieces (7) which are bonded on the surface of a cantilever beam (6) that is farthest along the direction of vibration from the neutral axis (S) of said beam (6) and near the fixed end (6b) so that said piezoelectric pieces (7) experience the maximum possible stress.

The voltage outputs, generated by the piezoelectric pieces (7) associated with each cantilever beam (6) vibrating near its natural frequency, are higher than a threshold voltage value which is the threshold voltage value required to stimulate the auditory nerve. The predetermined natural frequencies of the cantilever beams (6) correspond to the frequencies that a patient is unable to perceive. If the predetermined natural frequency of a cantilever beam (6) does not exactly correspond to the frequency of the relevant region of the auditory nerve, the nerve will in time adapt to respond perfectly to said cantilever beam (6).

Considering the most frequently encountered cases of sensorineural hearing loss, a spectrum build up of 1 to 30 different frequencies provides a fine coverage of the frequencies that cannot be perceived. Thus, for most patients, the number of cantilever beams (6) ranges from 1 to 30.

REFERENCES

[1] P. D. Mitcheson, et al., "Architectures for Vibration-Driven Micropower Generators", *Journal of Microelectromechanical Systems*, vol. 13, no. 3, Jun. 2004.
[2] C. B. Williams and R. B. Yates, "Analysis of micro-electric generator for microsystems", 8*th International Conference on Solid-State Sensors, Actuators, and Microsystems* (Transducers '95), Stockholm, pp. 369-372, Jun. 1995.
[3] S. Roundy, P. K. Wright and J. Rabaey, "A study of low level vibrations as a power source for wireless sensor nodes", *Computer Communications*, vol. 26, pp. 1131-1144, 2003.
[4] A. C. R. Grayson, et al., "A BioMEMS Review: MEMS Technology for Physiologically Integrated Devices", *Proceedings of the IEEE*, vol. 92, no. 1, Jan. 2004.
[5] A. Nisar, et al., "MEMS-based micropumps in drug delivery and biomedical applications", *Sensors and Actuators B:Chemical*, vol. 130, no.2, pp. 917-942, 2008.
[6] P. C. Loizou, "Introduction to Cochlear Implants", *IEEE Engineering in Medicine and Biology*, vol. 18, no. 1, pp. 32-42, Jan. 1999.
[7] B.S. Lee, et al., "Piezoelectric MEMS generators fabricated with an aerosol deposition PZT thin film", *Journal of Micromechanics and Microengineering*, vol. 19, no. 6, Jun. 2009.
[8] E. E. Aktakka, H. Kim and K. Najafi, "Wafer Level Fabrication Of High Performance MEMS Using Bonded And Thinned Bulk Piezoelectric Substrates", 15*th International Conference on Solid-State Sensors, Actuators, and Microsystems* (Transducers '09), Denver, pp. 849-852, Jun. 2009.
[9] M. K. Cosetti and S. B. Weitzman, "Cochlear implants: current status and future potential", *Expert Review of Medical Devices*, vol. 8, no. 3, pp. 389-401, May 2011.

The invention claimed is:

1. A cochlear implant, comprising:
    a transducer; and at least one cochlear electrode attached to auditory nerve;
    wherein the transducer further comprising: a plurality of cantilever beams and a piezoelectric piece bonded to each of the cantilever beams;
    wherein each of the plurality of cantilever beams has a different predetermined natural frequency from each other;
    each of the plurality of the cantilever beams comprises one free end and one fixed end; the piezoelectric piece is positioned on the fixed end;
    each of the plurality of cantilever beams is capable of converting incoming acoustic waves to voltage outputs through the piezoelectric piece;
    wherein the transducer is an energy harvester device having the capability of generating energy therefore reducing the need of battery to power up a cochlear implant;
    wherein the voltage outputs of the plurality of cantilever beams stimulates the corresponding auditory nerve; and
    wherein the voltage outputs generated by the piezoelectric piece associated with each cantilever beam vibrating near the natural frequency are higher than a threshold voltage value for stimulating the auditory nerve.

2. The cochlear implant of claim 1, wherein further comprises:
    at least one base attached onto a vibrating element of an auditory system that vibrates under the influence of the incoming acoustic waves; and
    at least one harvester electrode pair associated with each of the plurality of cantilever beams to harvest voltages produced by the piezoelectric pieces and to transmit the voltages to the at least one cochlear electrode, which stimulates the corresponding auditory nerve.

3. The cochlear implant of claim 1, wherein each of the plurality of the cantilever beams incorporates a tip mass on the free end tbr the predetermination of the natural frequency, wherein each tip mass comprises a rectangular structure with difference length.

4. The cochlear implant of claim 1, wherein the transducer comprises multiple bases having the plurality of cantilever beams of different natural frequencies, bonded on top of each other forming layers.

5. The cochlear implant of claim 4, wherein the number of the cantilever beams ranues from 1 to 30.

6. The cochlear implant of claim 1, wherein the transducer further comprises a biocompatible coating.

7. The cochlear implant of claim 1, wherein each voltage output corresponds to a particular frequency band of the incoming acoustic waves.

8. The cochlear implant of claim 1, wherein each of the plurality of cantilever beams comprises a rectangular structure with different length.

9. A method for converting acoustic waves to voltage outputs to stimulate auditory nerves by a cochlear implant of claim 1, wherein the method comprising the steps of:
   exposing the cantilever beams to vibrations produced on a vibrating element of the auditory system under the influence of the incoming acoustic waves; and
   generating the voltage outputs due to piezoelectricity, at the piezoelectric pieces associated with every vibrating cantilever beam;
   wherein predetermined natural frequencies of the plurality of the cantilever beams correspond to frequencies that a patient is unable to perceive.

* * * * *